United States Patent
Wu

(10) Patent No.: US 10,753,859 B2
(45) Date of Patent: *Aug. 25, 2020

(54) DUAL WAVELENGTH ISOELECTRIC FOCUSING FOR DETERMINING DRUG LOAD IN ANTIBODY DRUG CONJUGATES

(71) Applicant: ProteinSimple, Santa Clara, CA (US)

(72) Inventor: Jiaqi Wu, Woodbridge (CA)

(73) Assignee: ProteinSimple, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/793,434

(22) Filed: Oct. 25, 2017

(65) Prior Publication Data
US 2018/0136115 A1    May 17, 2018

Related U.S. Application Data

(63) Continuation of application No. 13/866,164, filed on Apr. 19, 2013, now Pat. No. 9,804,079.
(Continued)

(51) Int. Cl.
*G01N 21/25* (2006.01)
*G01N 21/31* (2006.01)
(Continued)

(52) U.S. Cl.
CPC ............ *G01N 21/25* (2013.01); *A61K 47/68* (2017.08); *G01N 21/31* (2013.01); *G01N 33/6854* (2013.01); *G01N 33/6857* (2013.01)

(58) Field of Classification Search
CPC .... G01N 21/25; G01N 21/31; G01N 33/6854; G01N 33/6857; A61K 47/68
(Continued)

(56) References Cited

U.S. PATENT DOCUMENTS

| 4,021,364 A | 5/1977 | Speiser et al. |
| 4,128,470 A | 12/1978 | Hiratsuka et al. |

(Continued)

FOREIGN PATENT DOCUMENTS

| CA | 2473925 A1 | 7/2003 |
| CA | 2559870 | 10/2005 |

(Continued)

OTHER PUBLICATIONS

Biorad Laboratories Inc., "A Guide to Polyacrylamide Gel Electrophoresis and Detection Begin," Jan. 1, 2011, Hercules, CA, Retrieved from the Internet: URL: http://www.bio-rad.com/webroot/web/pdf/lsr/literature/Bulletin_6040A.pdf [retrieved Mar. 3, 2015].

(Continued)

*Primary Examiner* — Rebecca M Fritchman
(74) *Attorney, Agent, or Firm* — Cooley LLP

(57) ABSTRACT

Provided herein are IEF focusing methods for determining the number of drug molecules present in at least one antibody-drug conjugate (ADC) species subpopulation. In one embodiment, the method comprises performing free solution isoelectric focusing on a sample comprising at least one ADC species, to obtain a focused sample. The absorbance of the sample at two different wavelengths is then measured, for example, over a range of pI values. Absorbance values at the two different wavelengths are compared at at least one corresponding pI value, where the at least one corresponding pI value is the pI of the ADC subpopulation. The number of drug molecules in the at least one ADC species subpopulation is then determined based on the comparison. The methods provided herein can also be used to determine the number of specific binding pair members bound to its target specific binding pair member.

20 Claims, 2 Drawing Sheets

Related U.S. Application Data

(60) Provisional application No. 61/635,616, filed on Apr. 19, 2012.

(51) Int. Cl.
*A61K 47/68* (2017.01)
*G01N 33/68* (2006.01)

(58) Field of Classification Search
USPC .......................................................... 436/86
See application file for complete search history.

(56) References Cited

U.S. PATENT DOCUMENTS

| | | |
|---|---|---|
| 4,716,101 A | 12/1987 | Thompson et al. |
| 4,788,138 A | 11/1988 | Tung et al. |
| 4,810,781 A | 3/1989 | Hollinshead |
| 4,843,010 A | 6/1989 | Nowinski et al. |
| 4,870,003 A | 9/1989 | Kortright et al. |
| 4,921,790 A | 5/1990 | O'Brien |
| 5,096,807 A | 3/1992 | Leaback |
| 5,106,951 A | 4/1992 | Morgan, Jr. et al. |
| 5,110,434 A | 5/1992 | Zhu et al. |
| 5,180,475 A | 1/1993 | Young et al. |
| 5,228,960 A | 7/1993 | Liu et al. |
| 5,244,813 A | 9/1993 | Walt et al. |
| 5,264,101 A | 11/1993 | Demorest et al. |
| 5,302,264 A | 4/1994 | Welch et al. |
| 5,348,633 A | 9/1994 | Karger et al. |
| 5,376,249 A | 12/1994 | Afeyan et al. |
| 5,468,359 A | 11/1995 | Pawliszyn |
| 5,482,867 A | 1/1996 | Barrett et al. |
| 5,505,831 A | 4/1996 | Liao et al. |
| 5,614,073 A | 3/1997 | Bobbitt et al. |
| 5,630,924 A | 5/1997 | Fuchs et al. |
| 5,633,129 A | 5/1997 | Karger et al. |
| 5,660,701 A | 8/1997 | Grushka et al. |
| 5,759,770 A | 6/1998 | Guertler et al. |
| 5,766,435 A | 6/1998 | Liao et al. |
| 5,804,384 A | 9/1998 | Mueller et al. |
| 5,840,503 A | 11/1998 | Beausang et al. |
| 5,858,188 A | 1/1999 | Soane et al. |
| 5,932,080 A | 8/1999 | Likuski |
| 5,963,456 A | 10/1999 | Klein et al. |
| 5,976,336 A | 11/1999 | Dubrow et al. |
| 5,976,896 A | 11/1999 | Kumar et al. |
| 6,037,138 A | 3/2000 | Moses et al. |
| 6,054,032 A | 4/2000 | Haddad et al. |
| 6,100,045 A | 8/2000 | Van Es |
| 6,107,038 A | 8/2000 | Choudhary et al. |
| 6,139,797 A | 10/2000 | Suzuki et al. |
| 6,375,817 B1 | 4/2002 | Taylor et al. |
| 6,475,364 B1 | 11/2002 | Dubrow et al. |
| 6,818,112 B2 | 11/2004 | Schneider et al. |
| 6,849,396 B2 | 2/2005 | Schneider |
| 6,852,206 B2 | 2/2005 | Pawliszyn et al. |
| 7,316,770 B2 | 1/2008 | Inaba et al. |
| 7,846,676 B2 | 12/2010 | Yang et al. |
| 7,935,308 B2 | 5/2011 | O'Neill et al. |
| 7,935,479 B2 | 5/2011 | O'Neill et al. |
| 7,935,489 B2 | 5/2011 | O'Neill et al. |
| 8,021,611 B2 | 9/2011 | Roach et al. |
| 8,945,361 B2 | 2/2015 | Gentalen et al. |
| 9,304,133 B2 | 4/2016 | O'Neill et al. |
| 9,377,440 B2 | 6/2016 | Wu et al. |
| 9,400,277 B2 | 7/2016 | Yang et al. |
| 9,804,079 B2 | 10/2017 | Wu |
| 2002/0071847 A1 | 6/2002 | Sadziene et al. |
| 2002/0110900 A1 | 8/2002 | Jovanovich et al. |
| 2002/0115740 A1 | 8/2002 | Beuhler et al. |
| 2003/0078314 A1 | 4/2003 | Johnson et al. |
| 2003/0128043 A1 | 7/2003 | Zeltz et al. |
| 2003/0148532 A1 | 8/2003 | Edwards et al. |
| 2004/0166546 A1 | 8/2004 | Warmington et al. |
| 2006/0057576 A1 | 3/2006 | Paszkowski et al. |
| 2008/0017512 A1 | 1/2008 | Bordunov et al. |
| 2008/0035484 A1 | 2/2008 | Wu et al. |
| 2008/0149484 A1 | 6/2008 | Tolley et al. |
| 2009/0023156 A1 | 1/2009 | Voss et al. |
| 2009/0194419 A1 | 8/2009 | Huang et al. |
| 2010/0089753 A1 | 4/2010 | Edwards et al. |
| 2011/0011740 A1 | 1/2011 | Roach et al. |
| 2011/0139622 A1 | 6/2011 | Tolley et al. |
| 2012/0322686 A1* | 12/2012 | Lyon ..................... C07K 16/00 506/9 |
| 2013/0280815 A1 | 10/2013 | Wu |
| 2015/0090591 A1 | 4/2015 | Yang et al. |
| 2015/0093757 A1 | 4/2015 | Gavin |

FOREIGN PATENT DOCUMENTS

| | | |
|---|---|---|
| CA | 2806640 | 2/2012 |
| EP | 0805215 A | 11/1997 |
| JP | 05-172815 A | 7/1993 |
| WO | WO 94/12871 | 6/1994 |
| WO | WO 99/63408 | 12/1999 |
| WO | WO 2001/055721 | 8/2001 |
| WO | WO 2003/062827 | 7/2003 |
| WO | WO 2003/100086 | 12/2003 |
| WO | WO 2011/109308 | 9/2011 |

OTHER PUBLICATIONS

Bossi, A. et al., "Capillary Electrophoresis Coupled to Biosensor Detection," J. Chromatography A, 892:143-153 (2000).

Breau, A. et al., "Evaluating the bioequivalence of antibody-drug conjugates," Pharmaceutical Technology, Analytical Technology & Testing, pp. s22-s27 (2011).

Chandler, J. P., "Purification and characterization of antibodies," pp. 125-155 (2006).

Chang, W., et al., "Enhanced Resolution Achieved with Electroosmotic Flow Control in Capillary Isoelectric Focusing with Dynamic Coatings," *Am. Biotechnology. Lab.* (2005).

Chen, X. et al., "Charge-based analysis of antibodies with engineered cysteines From multiple peaks to a single main peak," MABS, Landes Bioscience, 1(6):563-571 (2009).

Cruickshank, K., et al. "Simultaneous Multiple Analyte Detection Using Fluorescent Peptides and Capillary Isoelectric Focusing," Journal of Chromatography A, 817:41-47 (1998).

He, X. Z. et al., "Analysis of charge heterogeneities in mAbs using imaged CE," Electrophoresis, 30(5):714-722 (Mar. 2009).

Michels, D. A. et al., "Imaged capillary isoelectric focusing for charge-variant analysis of biopharmaceuticals," BioProcess International, 9(10):48-54 (Nov. 2011).

Misiakos et al., "A Multi-Band Capillary Immunosensor," Biosensors & Bioelectronics, 13:825-830 (1998).

Narang et al., "Multianalyte Detection Using a Capillary-Based Flow Immunosensor," Anal. Biochem., 225:13-19 (1998).

O'Neill, R. A. et al., "Isoelectric Focusing Technology Quantifies Protein Signaling in 25 Cells," PNAS, 103:16153-16158 (2006).

Rooseboom, M. et al., "Enzyme-catalyzed activation of anticancer prodrugs," Pharmacological Reviews, 56(1):53-102 (2004).

Scatchard, G., "The attractions of proteins for small molecules and ions," Ann. N.Y. Acad. Sci., 51:660-672 (1949).

Shang, T. Q., "Carrier ampholyte-free solution isoelectric focusing as a prefractionation method for the proteomic analysis of complex protein mixtures," Electrophoresis, 24:2359-2368 (2003).

Sosic, Z. et al., "Application of imaging capillary IEF for characterization and quantitative analysis of recombinant protein charge heterogeneity," Electrophoresis, 29(21):4368-4376 (Nov. 2008).

Vilkner, T. et al., "Micro Total Analysis Systems. Recent Developments," Analytical Chemistry, 76(12):3373-3385 (2004).

Wakankar, A. et al., "Analytical methods for physicochemical characterization of antibody drug conjugates," Landes Bioscience, 3(2):161-172 (2011).

Wang et al., "Enhancement of the Sensitivity of a Capillary Electrophoresis Immunoassay for Estradiol with Laser-Induced Fluorescence Based on a Fluorescein-labeled Secondary Antibody," Anal. Chem., 2001, 73:5616-5619.

(56) References Cited

OTHER PUBLICATIONS

Wu, J. et al., "Capillary isoelectric focusing with whole column detection and a membrane sample preparation system," Analytica Chimica Acta, 383(1-2):67-78 (1999).
Zhu, Z. et al., "Protein separation by capillary gel electrophoresis: a review," Analytica Chimica Acta, 709:21-31 (Oct. 2011).
Extended European Search Report for European Application No. 13778992.1, dated Dec. 7, 2015, 10 pages.
Office Action for U.S. Appl. No. 13/866,164, dated Feb. 20, 2015, 7 pages.
Office Action for U.S. Appl. No. 13/866,164, dated Dec. 1, 2015, 9 pages.
Office Action for U.S. Appl. No. 13/866,164, dated Jun. 29, 2016, 10 pages.
Office Action for U.S. Appl. No. 13/866,164, dated Feb. 17, 2017, 12 pages.
International Search Report and Written Opinion for International Application No. PCT/CA2013/050304, dated Jul. 24, 2013, 9 pages.
International Preliminary Report on Patentability for International Application No. PCT/CA2013/050304, dated Oct. 21, 2014, 7 pages.
Wang, L, et al., "Detection of Target Proteins by Fluorescence Anisotropy," J. Fluoresc. (2013) 23:881-888.

\* cited by examiner

DUAL WAVELENGTH ISOELECTRIC FOCUSING FOR DETERMINING DRUG LOAD IN ANTIBODY DRUG CONJUGATES

CROSS REFERENCE TO RELATED APPLICATIONS

This application is a continuation of U.S. patent application Ser. No. 13/866,164, filed Apr. 19, 2013, which claims the benefit of U.S. Provisional Patent Application No. 61/635,616, filed on Apr. 19, 2012, each entitled "DUAL WAVELENGTH ISOELECTRIC FOCUSING FOR DETERMINING DRUG LOAD IN ANTIBODY DRUG CONJUGATES," the disclosures of each of which are incorporated herein by reference in their entirety.

BACKGROUND OF THE INVENTION

Chemotherapy has been used, with varying success, in the treatment of metastatic cancers. However, a major problem with many chemotherapeutic agents is their damage to normal cells and organs, poor selectivity for neoplastic cells and multidrug resistance upon prolonged treatment (Rooseboom et al. (2004). Pharmaceutical Reviews 56, pp. 53-102).

One strategy to overcome the limitations of chemotherapeutic agents is to conjugate one or more agents to an antibody, which is specific for a cell type or tissue. Antibody-drug conjugates (ADCs) have been used as a more rational approach to targeting cytotoxic agents to cells. Both polyclonal and monoclonal antibodies can be used in ADCs. In an ADC, one or more drug molecules are covalently bonded to an antibody (or fragment thereof).

ADCs have been used to enhance the antitumor activity of antibodies as well as to reduce the systemic toxicity of drugs. Antibody targeted therapy is advantageous because the epitope(s) recognized by the antibody is typically overexpressed on a tumor cell, or only expressed on the tumor cell. Therefore, conjugating a drug (e.g., a chemotherapeutic agent) to an antibody allows the delivery of the drug, to the tissue or specific cell type of interest. The antibody portion of the conjugate specifically binds the target of interest, while the drug portion of the conjugate exerts its effects in the cell tissue to which the antibody binds. Once the antibody is bound to the target cell-surface antigen, the conjugate is processed to release an active form of the drug, which can reach its intracellular target.

Although ADCs have been used in cancer therapy, rapid and reliable methods are lacking for determining the amount of drug molecule present in an ADC complex. The present invention addresses this and other needs.

SUMMARY OF THE INVENTION

In one aspect, the present invention is directed to IEF focusing methods for determining the number of drug molecules present in at least one antibody-drug conjugate (ADC) species subpopulation. In one embodiment, the method comprises performing free solution isoelectric focusing on a sample comprising at least one ADC species, to obtain a focused sample. The absorbance of the sample at two different wavelengths is then measured, for example, over a range of pI values. Absorbance values at the two different wavelengths are compared at at least one corresponding pI value, where the at least one corresponding pI value is the pI of the ADC subpopulation. The number of drug molecules in the at least one ADC species subpopulation is then determined based on the comparison.

In one aspect, the present invention is directed to IEF focusing methods for determining the number of specific binding pair members bound to its target specific binding pair member. In one embodiment, the method comprises performing free solution isoelectric focusing on a sample comprising at least one specific binding pair species, to obtain a focused sample. The absorbance of the sample at two different wavelengths is then measured, for example, over a range of pI values. Absorbance values at the two different wavelengths are compared at at least one corresponding pI value, where the at least one corresponding pI value is the pI of the specific binding pair. The number of specific binding pair members in the at least one specific binding pair is then determined based on the comparison.

In one embodiment, the methods provided herein are performed in a capillary tube. In a further embodiment, the free solution isoelectric focusing is performed with $H_3PO_4$ as the anolyte. In even a further embodiment, the free solution isoelectric focusing is performed with NaOH as the catholyte.

As provided above, in one embodiment, absorbance of the focused sample is measured at two different wavelengths. In one embodiment, the absorbance of the sample is measured at one ultraviolet wavelength and one visible wavelength. In one embodiment, the absorbance of the sample is measured at two different ultraviolet wavelengths. In one embodiment, absorbance is measured over a range of pH values, e.g., from about 2 to about 12, or about 2 to about 11, or about 6 to about 12, by a whole column detection method. In this regard, multiple absorbance values can be taken over a range of pI values, instead of single readings at single pI values. In one embodiment, absorbance values at corresponding pI peaks, measured at the two different wavelengths are compared to determine the amount of drug loaded onto an antibody in an ADC.

In another embodiment, a method is provided for determining the number of drug molecules in an ADC subpopulation in a sample comprising a plurality of at least one ADC population. The method comprises performing free solution isoelectric focusing on a sample comprising a plurality of at least one ADC species, to obtain a focused sample. The absorbance of the sample is then measured at two wavelengths, e.g., (i) from about 220 nm to about 300 nm and (ii) from about 280 nm to about 700 nm. The ratio of absorbance values at a corresponding pI value, in one embodiment, provides a number of drug molecules loaded onto the antibody.

In yet another embodiment, a method is provided for determining the number of drug molecules in an ADC subpopulation in a sample comprising at least two different ADC species. In a further embodiment, the first ADC species comprises a drug with a higher net charge than the second ADC species. In a further embodiment, the method comprises performing free solution isoelectric focusing on the sample, to obtain a focused sample. The absorbance of the sample is then measured at three different wavelengths via a whole column detection method. For example, in one embodiment, the three wavelengths are (i) from about 220 nm to about 300 nm, (ii) from about 280 nm to about 700 nm and (iii) from about 280 nm to about 700 nm. Each of the absorbance values (ii) and (iii) can then be compared separately to the absorbance value (i), for example at at least one corresponding pI value, to determine the amount of drug present in a particular ADC complex. In one embodiment, at least one of the wavelengths is an ultraviolet wavelength.

In another aspect, the present invention is directed to a method of determining the number of ADC subpopulations in a sample. In a further embodiment, the concentration of each subpopulation is determined.

DETAILED DESCRIPTION OF THE INVENTION

Figure 1:
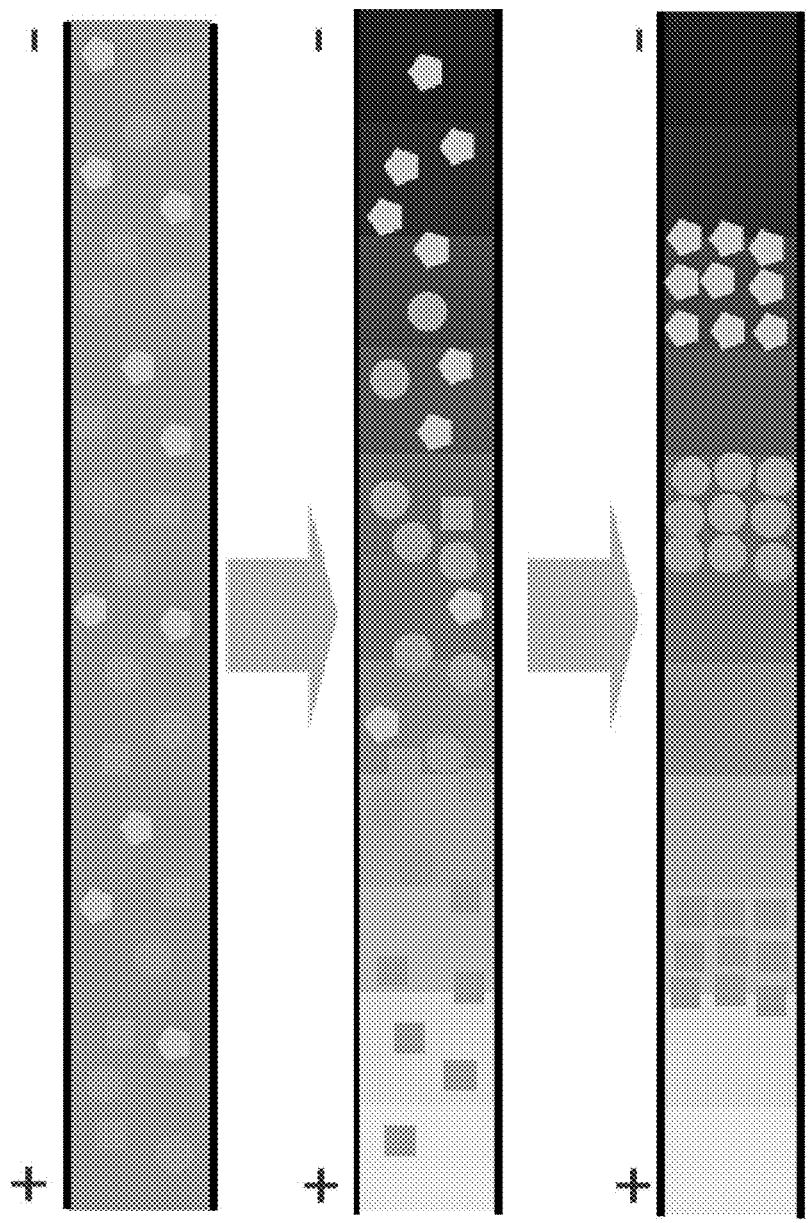
FIG. 1 is a schematic of an isoelectric focusing process.

Current methods are lacking for determining the number of drug molecules bound to an antibody in an ADC, as well as the amount of free drug in sample comprising ADCs. The present invention addresses this and other needs. Additionally, the present invention provides analytical methods for determining the number of specific binding pair members bound to its target specific binding pair member, in a sample comprising at least one specific binding pair. In this regard, the methods provided herein are useful for determining the percentage of bound specific binding pair member in a sample. In the case of specific binding pair members with a plurality of binding sites, the present invention provides methods for determining the percentage of binding sites occupied on the respective target specific binding pair member.

As used herein, the term "antibody" and "antibodies" can include, but is not limited to, polyclonal antibodies, monoclonal antibodies, human antibodies, humanized antibodies, chimeric antibodies, single-chain Fvs (scFv), single chain antibodies, Fab fragments, F(ab') fragments, disulfide-linked Fvs (sdFv), anti-idiotypic (anti-Id) antibodies (e.g., anti-Id antibodies to antibodies of the disclosure), and epitope-binding fragments of any of the above (i.e., antigen binding fragments). In particular, antibodies include immunoglobulin molecules and immunologically active fragments of immunoglobulin molecules (i.e., molecules that contain an antigen binding site). Immunoglobulin molecules can be of any type (e.g., IgG, IgE, IgM, IgD, IgA and IgY), class (e.g., IgG1, IgG2, IgG3, IgG4, IgA1 and IgA2) or subclass. The antibodies may be from any animal origin including birds and mammals (e.g., human, murine, donkey, sheep, rabbit, goat, guinea pig, camel, horse, or chicken).

"Free drug" as used herein, means a drug molecule that is not conjugated to an antibody.

As used herein, "antibody-drug conjugate species" or "ADC species", means an ADC comprising a molecule or modification unique to the ADC. For example, one ADC species, in one embodiment, comprises a drug that is different from the drug in another ADC species. In another embodiment, one ADC species comprises an antibody that is different from the antibody in another ADC species, e.g., an antibody with a different amino acid sequence. The total number of an ADC species in a sample is referred to herein as an ADC population.

"An ADC subpopulation", as used herein, refers to ADCs of the same species, where each subpopulation has a different number of drug molecules conjugated to the antibody. For example, one ADC species may have five different subpopulations, e.g., (1) an ADC with one drug molecule conjugated to the antibody, (2) an ADC with two drug molecule conjugated to the antibody, (3) an ADC with three drug molecules conjugated to the antibody, (4) an ADC with four drug molecules conjugated to the antibody, (5) an ADC with five drug molecules conjugated to the antibody. In one embodiment, the present invention provides methods for determining the number of subpopulations of ADCs, i.e., methods for differentiating between ADCs in a sample with varying conjugation levels. The subpopulations, in one embodiment, are quantified to determine the concentration of ADC subpopulations in the sample.

A "specific binding pair" is a pair of molecules (each a "specific binding pair member") which are naturally derived or synthetically produced. One member of the pair of molecules ("target specific binding pair member") has an area on its surface, or a cavity which specifically binds to, and is therefore defined as complementary with a particular spatial and polar organization of the other molecule in the pair, so that the pair have the property of binding specifically to each other. Examples of types of specific binding pairs are antigen-antibody, biotin-avidin, hormone-hormone receptor, receptor-ligand, enzyme-substrate, IgG-protein A. In one embodiment, the specific binding pair comprises an antibody (or antigen binding portion thereof) and a drug, i.e., an antibody-drug conjugate (ADC).

A "specific binding pair member" according to the invention can be, for example, a protein, a peptide, nucleic acid, carbohydrate, lipid, or small molecule compound that binds specifically to a target molecule, i.e., the second member of the binding pair. In the methods provided herein, in one embodiment, the non-target specific binding pair member has a net charge, e.g., a charged antigen or a charged ligand.

A specific binding pair member is specific for the second member of the binding pair if it binds to the second member with a greater affinity than any other target. For example, an antibody binds to its antigen with a greater affinity than to any other target. Binding molecules of the invention may have affinities for their targets of a Ka of greater than or equal to about $10^4$ $M^{-1}$, greater than or equal to about $10^5$ $M^{-1}$, greater than or equal to about $10^6$ $M^{-1}$ or greater than or equal to about $10^7$ $M^{-1}$. Affinities of even greater than about $10^7$ $M^{-1}$ are also within the scope of the invention, for example, affinities equal to or greater than about $10^7$ $M^{-1}$, about $10^8$ $M^{-1}$, about $10^9$ $M^{-1}$, and about $10^{10}$ $M^{-1}$. Affinities of binding molecules according to the present invention can be readily determined using conventional techniques, for example those described by Scatchard et al., Ann. N.Y. Acad. Sci. 51:660 (1949).

Isoelectric focusing (IEF) methods are provided herein for the separation of various molecules, including proteins and protein conjugates (e.g., antibody-drug conjugates) as well as specific binding pair members, and specific binding pairs. The components of a sample undergoing isoelectric focusing in a pH gradient migrate towards the anode or the cathode to the respective pH value where the component's net charge is zero, i.e., the component's isoelectric point (pI). IEF is therefore a mode of electrophoresis for amphoteric molecules. However, it separates molecules based on their pI values, in contrast to other electrophoresis techniques which typically utilize some form of size-based separation. IEF can also be used as a concentrating technique since molecules having the same pIs are focused into narrow zones in the pH gradient. In this regard, molecules with the same pI can be quantified in the sample, by measuring the absorbance of the sample at respective pI. At the end of the separation, the zones are stationary.

Traditional IEF is performed in polyacrylamide slab gels. First, a pH gradient is created on the slab gel by carrier ampholytes under a separation voltage. Then, protein samples are loaded into the gel to start the separation.

Although slab gel IEF has high resolution for protein separation, it tends to be slow, labor intensive, and not quantitative. As an alternative to IEF performed in polyacrylamide slab gels, IEF performed in a column format allows for high resolution detection. Additionally, column-based IEF is advantageous in terms of automation and separation speed.

To this end, column based capillary isoelectric focusing (cIEF), also referred to as "free solution isoelectric focusing", is currently employed as a separation technique for proteins and peptides due to its fast separation speed and ease of use for quantitative determination. In cIEF applications, sample and carrier ampholytes (CA) are injected into the capillary (FIG. 1). The CA forms a pI gradient across the capillary and species migrate according to its respective pI. Eventually, species focus at the pH where its charge is neutral (FIG. 1).

For example, the iCE280 System and the iCE3 System (ProteinSimple, Santa Clara, Calif.) performs free solution IEF in a capillary column (cIEF) and detects focused protein zones using a whole column UV absorption detector that avoids disturbing these focused zones. Both whole column detection and a combination of whole column detection/single pI detection are amenable for the methods described herein, as discussed further below.

Most applications of cIEF have been done using commercial capillary electrophoresis (CE) instruments. These instruments have a 20-60 cm long capillary and an on-column UV absorption detector. When using these instruments for cIEF, all protein zones separated by the focusing process must be moved through the detection point of the on-column detector located at one end of the capillary, i.e., a mobilization step must be employed.

In conventional cIEF, as provided above, after the isoelectric focusing process, a mobilization process is necessary to move all the focused protein zones past the detection point of the on-column detector in order to detect these zones. The mobilization process introduces problems such as poor resolution, poor reproducibility and long sample analysis times (for example, less than 2 samples/hour). Therefore, in conventional cIEF, the dynamic process of IEF within the separation column is not monitored.

In one aspect, the present invention is directed to IEF methods for determining the number of drug molecules bound to an antibody in an ADC, wherein the sample comprises at least one ADC species. In another aspect, the present invention is directed to IEF methods for determining the percentage of free drug in a sample, wherein the sample comprises at least one antibody-drug conjugate species. In another aspect, the present invention is directed to IEF methods for determining the number of specific binding pair members bound to its respective target specific binding pair member.

In even another aspect, the present invention is directed to IEF methods for determining the percentage of a free specific binding pair member in a sample, wherein the sample comprises at least one specific binding pair species. In this aspect, the free specific binding pair member is charged, e.g., a charged antigen or a charged ligand.

In one embodiment, the methods provided herein comprise performing free solution isoelectric focusing on a sample comprising at least one ADC population (e.g., in a capillary tube) to obtain a focused sample.

Figure 2:
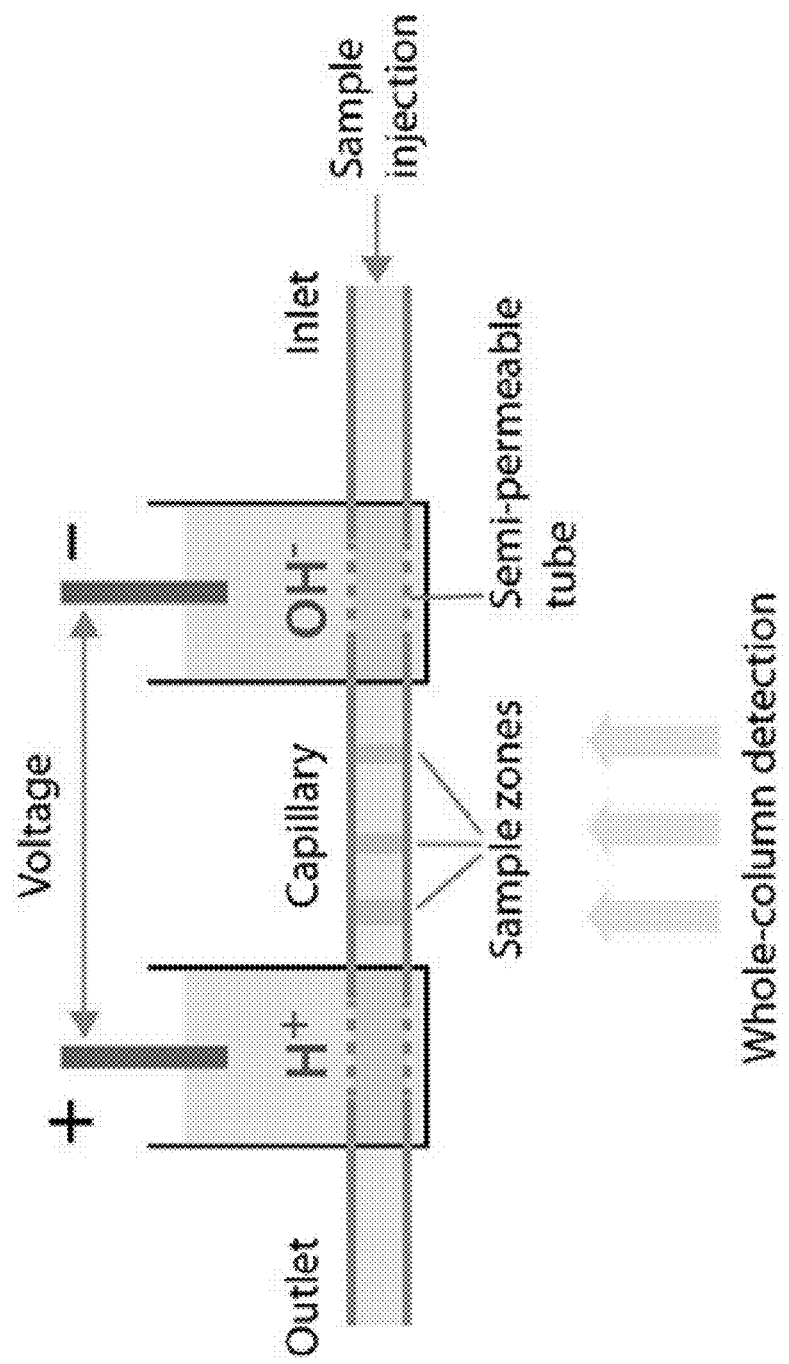
FIG. 2 is a schematic of a capillary IEF (cIEF) instrument that can be used to carry out embodiments of the methods described herein.

In one embodiment, the free drug molecule has a net charge. In this regard, a shift in pI values is observed based on the number of drug molecules bound to the antibody. In one embodiment, the methods provided herein can distinguish different ADC species based on the ADC's isoelectric shift (shift in pI). For example, an ADC species comprising a drug with a higher net charge than a second ADC species will migrate to a different pI. In one embodiment, the absorbance is measured over a range of pIs via a whole column detection method (FIG. 2). In one embodiment, a method is provided herein to determine the amount or percentage of free drug in a sample comprising a population of ADCs. In another embodiment, a method is provided to determine the number of ADC species in a sample.

In one embodiment, the concentration of at least one ADC subpopulation is determined by the methods provided herein. In another embodiment, the number of drug molecules present in an ADC is determined.

Absorbance of the sample is measured at at least two different wavelengths. In one embodiment, the absorbance of the sample is measured at two wavelengths, where one wavelength is an ultraviolet wavelength. In a further embodiment, the absorbance of the sample is measured at two ultraviolet wavelengths or one ultraviolet wavelength and one visible wavelength. In one embodiment, absorbance is measured (i) at a wavelength from about 220 nm to about 300 nm and (ii) at a wavelength from about 280 nm to about 700 nm.

One absorbance value is specific for the drug molecule, i.e., protein (e.g., antibody) absorbance is minimal to undetectable at this wavelength. The absorbance measurement for the drug molecule, in one embodiment, is taken at a wavelength from about 280 nm to about 700 nm, from about 280 nm to about 600 nm, from about 280 nm to about 500 nm, from about 280 nm to about 400 nm or from about 280 nm to about 350 nm. The absorbance measurement for the drug molecule, in another embodiment, is taken at a wavelength from about 310 nm to about 700 nm, from about 350 nm to about 700 nm, from about 400 nm to about 700 nm, from about 450 nm to about 700 nm, from about 500 nm to about 700 nm, from about 550 nm to about 700 nm, from about 600 nm to about 700 nm or from about 650 nm to about 700 nm. As provided above, protein (e.g., antibody) absorbance may be detectable at the absorbance reading for the drug molecule. In these instances, antibody absorbance can be subtracted from the drug molecule scan based on the second scan (i.e., the protein reading, discussed below).

In one embodiment, the absorbance reading for the drug molecule is carried out over a range of pI values, by whole column detection. In another embodiment, if the pI value of the drug is known, a single absorbance reading can be taken at that respective pI value. In one embodiment, absorbance values for the drug at multiple pI values are taken and compared to corresponding absorbance values at a second wavelength where drug molecule absorbance is minimal to undetectable (i.e., at the same or about the same pI values), to determine the amount of drug loaded onto an antibody in an ADC species.

It should be noted that for the drug molecule absorbance reading, absorbance of the drug is detectable where the drug is present in an ADC. Because protein absorbance is minimal at the drug molecule reading, absorbance values at the drug molecule reading can be used to calculate the concentration and/or number of drug molecules present in an ADC, for example, by determining absorbance at various pI values at two different wavelengths. In this regard, it is possible to determine the number of drug molecules in an ADC subpopulation, and also the distribution of drug molecules in multiple ADC subpopulations.

The second (protein, e.g., antibody) reading, in one embodiment, is carried out at a wavelength where the protein (e.g., antibody) absorbs ultraviolet light, e.g., from about 220 nm to about 300 nm. At this wavelength, drug molecule absorbance is not detectable or is minimal. Additionally, because ADC subpopulations migrate to different pIs when subjected to isoelectric focusing, in one embodiment, absorbance peaks will be present that correspond to different ADC subpopulations.

The protein (e.g., antibody) absorbance measurement in one embodiment, is taken at a wavelength from about 220 nm to about 300 nm, from about 230 nm to about 300 nm, from about 240 nm to about 300 nm, from about 250 nm to about 300 nm, from about 260 nm to about 300 nm, from about 270 nm to about 300 nm or from about 280 nm to about 300 nm. The protein (e.g., antibody) absorbance measurement in another embodiment, is taken at a wavelength from about 220 nm to about 290 nm, from about 220 nm to about 280 nm, from about 220 nm to about 270 nm, from about 220 nm to about 260 nm, from about 220 nm to about 250 nm or from about 220 nm to about 240 nm.

The protein absorbance reading is taken over a range of pI values, e.g., via a whole column detection method. This allows for the determination of whether multiple ADC subpopulations are present in the sample, as well as the determination of one or more of the ADC subpopulations present in the sample. Absorbance values at at least one corresponding pI value, in one embodiment, are compared to determine the number of drug molecules present in an ADC subpopulation. In this embodiment, the pI value where absorbance is compared is the pI value of the ADC subpopulation. In a further embodiment, absorbance values at multiple corresponding pI values are compared, to determine the number of drug molecules present in multiple ADC subpopulations.

In another embodiment, the cumulative ADC absorbance (i.e., the absorbance of each of the subpopulations of ADCs), is compared to the absorbance value of the free drug to determine the percentage of free drug in solution. The ratio also provides the percentage of drug load in the ADC species population.

In one embodiment, absorbance peaks in the protein reading are compared to corresponding peaks in the drug molecule reading. Corresponding peaks refer to peaks at the same or about the same pI value. The number of drug molecules loaded onto an antibody in an ADC is determined, in one embodiment, by comparing absorbance values at one or more corresponding pI values. Here, the one or more pI values correspond to the pIs of the ADC subpopulations in the sample. The absorbance values for the corresponding peaks at the two wavelengths, in one embodiment, provide a measure of the distribution of drug molecule in the ADC species population.

In one embodiment, multiple ADC species, i.e., multiple ADC populations are present in the sample, and each species includes a drug molecule with a different net charge. In this embodiment, the methods provided herein comprise performing free solution isoelectric focusing on the sample (e.g., in a capillary tube) to obtain a focused sample. Absorbance of the sample is then measured at three different wavelengths. In one embodiment, one of the three wavelengths is an ultraviolet wavelength, while the other two wavelengths may be in the visible or ultraviolet regions of the electromagnetic spectrum. Suitable wavelengths for absorbance measurements are provided above. One absorbance reading is specific for the protein (e.g., antibody), and drug molecule absorbance is minimal or non-detectable at this wavelength. The protein reading, in one embodiment, is carried out at a wavelength where the protein (e.g., antibody) absorbs ultraviolet light, e.g., from about 220 nm to about 300 nm. At this wavelength, drug molecule absorbance is not detectable or is minimal and therefore can be subtracted. The protein absorbance reading is taken over a range of pI values, e.g., via a whole column detection method to determine the absorbance of one or more ADC species subpopulations present in the sample.

One absorbance value is taken at a visible or ultraviolet wavelength (e.g., a wavelength from about 280 nm to about 700 nm), and is specific for the first drug molecule, i.e., protein absorbance and second drug molecule absorbance is minimal to undetectable at this chosen wavelength. The other absorbance reading is taken at a visible or ultraviolet wavelength (e.g., a wavelength from about 280 nm to about 700 nm), and is specific for the second drug molecule, i.e., protein absorbance and first drug molecule absorbance is minimal to undetectable at this chosen wavelength. In one embodiment, the absorbance readings for the drug molecules are carried out over a range of pI values, by whole column detection.

In one embodiment, the absorbance reading for the first or second drug molecule is compared to the protein absorbance reading at a corresponding pI value to determine the number of drug molecules present in an ADC subpopulation. The pI value is the pI of the ADC subpopulation. In a further embodiment, the absorbance reading for the first or second drug molecule is compared to the protein absorbance reading at a plurality of corresponding pI value to determine the number of drug molecules present in a plurality of ADC subpopulations.

In one embodiment, the cumulative ADC absorbance (i.e., the absorbance of each of the subpopulations of ADCs), is compared to the absorbance value for each of the drug molecules to determine the percentage of the individual drug molecules in solution.

The cumulative ADC absorbance, in another embodiment, is compared to cumulative drug absorbance, to determine the percentage of total free drug in the sample.

In another embodiment, corresponding absorbance peaks (i.e., at corresponding pI values) at the first drug molecule wavelength and the protein wavelength are compared to determine the distribution of first drug molecule in the sample or the number of first drug molecules present in a particular ADC subpopulation. One or more comparisons can be carried out, depending on the number of ADC subpopulations present in the sample.

In yet another embodiment, corresponding (i.e., at a corresponding pI value) absorbance peaks at the second drug molecule wavelength and the protein wavelength are compared to determine the number of second drug molecules present in a particular ADC subpopulation. One or more comparisons can be carried out, depending on the number of ADC subpopulations present in the sample. The number of ADC subpopulations can be determined, for example, by determining the number of corresponding absorbance peaks.

It should be noted that in the methods described herein, the wavelength absorbance measurements can be carried out in any order.

In one embodiment, the methods provided herein employ whole column detection. In this embodiment, absorbance values are determined over a range of pI values, for example pI from about 5 to about 11, or about 6 to about 10, or about 7 to about 10.

In one embodiment, whole column detection is used in the methods described herein. One schematic of a capillary IEF (cIEF) instrument that can be used to carry out the methods described herein is provided in FIG. 2. In one embodiment, one of the cIEF instruments disclosed in U.S. Pat. Nos. 5,784,154, 5,395,502, 5,468,359 or 5,985,121 is used or modified to carry out the methods of the present invention. One of ordinary skill in the art will recognize that for the multi-wavelength methods, (e.g., dual-wavelength or tri-wavelength) the optics in the instruments will in some instances, need modification, i.e., to enable absorbance readings at at least two different wavelengths or at least three different wavelengths. For example, an additional filter(s) can be added to the optics of one of the instruments described or referenced herein, and the optics can also be realigned, if necessary. Each of U.S. Pat. Nos. 5,784,154, 5,395,502, 5,468,359 or 5,985,121 is incorporated herein by reference for all purposes.

As described above, in one aspect, the present invention is directed to IEF focusing methods for measuring the number of drug molecules present in an ADC subpopulation. In another aspect, methods provided herein allow for the determination of the distribution of drug molecules in an ADC species population. In some instances, the amount of free drug in the sample is also discernable with the methods provided herein. ADCs can be synthesized with a varying number drug molecules conjugated to the antibody surface, and therefore, it is beneficial to determine the identity of ADC subpopulations as well as the concentration of drug in ADC subpopulations in a sample of ADCs.

In one embodiment, the present invention provides methods for determining the number of subpopulations of ADCs in a sample. In one embodiment, the number of overlapping absorbance peaks provides the number of ADC subpopulations in the sample. The concentrations of the subpopulations, in one embodiment, are quantified, e.g., via Beer's law, to determine the concentration of different ADC subpopulations in the sample. In one embodiment, quantification of ADC subpopulations is carried out in addition to determining the number of drug molecules in a particular ADC subpopulation.

As stated above, the isoelectric focusing methods described herein can be used to differentiate between ADC subpopulations in a sample, e.g., subpopulations of ADCs that include one drug molecule, two drug molecules, three drug molecules, four drug molecules, five drug molecules, six drug molecules, seven drug molecules, eight drug molecules, nine drug molecules or ten drug molecules conjugated to the particular antibody. Depending on how many drug molecules are contemplated in an ADC, one of ordinary skill in the art will know what type of reagents to employ in the IEF method, e.g., a determination as to which ampholyte solution to use will be apparent.

In one cIEF embodiment, protein samples (e.g., ADCs and/or specific binding pairs) are first premixed with carrier ampholytes, additives and pI markers.

pI markers are available commercially, and for a range of pIs, for example from ProteinSimple (Santa Clara, Calif.). One of ordinary skill in the art, depending on the conjugate or complex in the sample, will readily know the pI marker, or multiple pI markers to employ. In one embodiment, at least two or at least three pI markers are added to the sample prior to isoelectric focusing.

Carrier ampholytes are used to generate a pH gradient. An ampholyte is a molecule with both at least once basic and at least one acidic group. Carrier ampholytes are a mixture of amphoteric compounds numbering in the thousands, and are used to generate a stable pH gradient in isoelectric focusing methods. The present invention is not limited by the type of carrier ampholyte.

For example, Servalyts™ (Serva), Biolytes (Bio-Rad), Zoom® (Invitrogen), Ampholines™ (GE) and Pharmalytes® are amenable for use with the methods disclosed herein.

Carrier ampholytes are available based on the pH range of the composition. Therefore, depending on the pH gradient required, one carrier ampholyte may be desired over another, e.g., a carrier ampholyte having the pH range of 3.5-9.5 vs. a carrier ampholyte having a pH range of 2-11.

In one embodiment, the sample comprises about 5% to about 10% pH 3-10 ampholytes. In another embodiment, the sample comprises about 8% pH 3-10 ampholytes. In yet another embodiment, the sample comprises about 2% pH 8-10.5 ampholytes. In another embodiment, the sample comprises about 5% to about 10% pH 2-9 ampholytes. In even another embodiment, the sample comprises about 8% pH 2-9 ampholytes.

One of ordinary skill in the art, depending on the particular sample, will readily know which carrier ampholyte to employ. For example, in one embodiment, it may be desirable to focus a sample over a wider range of pH values because the sample may contain many ADC subpopulations (e.g., 5, 10, 15 or 20 subpopulations).

The sample mixture (e.g., comprising protein sample, carrier ampholytes, additives, pI markers) is injected to fill the entire capillary column. A separation voltage is applied to the anolyte and catholyte tanks. In one embodiment, the separation is carried out at about 100 V/cm to about 1000 V/cm, or about 100 V/cm to about 900 V/cm, or about 100 V/cm to about 800 V/cm, or about 100 V/cm to about 700 V/cm, or about 100 V/cm to about 600 V/cm, or about 100 V/cm to about 500 V/cm. In one embodiment, separation is carried out at about 400 V/cm, or about 500 V/cm, or about 600 V/cm, or about 700 V/cm. In a further embodiment, separation is carried out about 600 V/cm.

Under the voltage, a pH gradient is created within the column. Proteins are separated and focused along the capillary column (FIGS. 1, 2). The whole-column detector (FIG. 1) monitors the IEF process in an on-line fashion within the separation column, and the focusing time, in one embodiment, is optimized in a single sample run. At the end of the focusing process, all the focused protein zones within the column are recorded by the detector without disturbing the separation resolution. Finally, the column is washed and ready for the next sample injection.

If precipitation and aggregation are evident, different additives may be included in the protein sample to improve reproducibility.

The methods provided herein, in one embodiment, employ whole column detection schemes. In this regard, absorbance values are determined over a range of pIs, rather than a single or a few pIs (FIG. 2).

In another embodiment, the amount of free drug in a sample is determined via single-point capillary isoelectric focusing (cIEF) detection. In a further embodiment, one of the multiple absorbance readings is carried out at a single pI (i.e., free drug reading), and one absorbance reading is carried out via a whole column detection method.

In one embodiment, sample detection is carried out at multiple different wavelengths, for example two different wavelengths. In this embodiment, one reading (the antibody or protein reading) is taken at a wavelength from about 220 nm to about 300 nm, or about 230 nm to about 300 nm, or about 240 nm to about 300 nm, or about 250 nm to about 300 nm, or about 260 nm to about 300 nm, or about 270 nm to about 300 nm. In a further embodiment, one reading (antibody or protein reading) is taken at about 220 nm, about 230 nm, about 240 nm, about 250 nm, about 260 nm, about 270 nm, about 280 nm, about 290 nm or about 300 nm.

The second reading (drug molecule reading) is taken at a different wavelength than the protein reading. For example, the second reading is taken at a wavelength in either the visible or ultraviolet region of the electromagnetic spectrum. For example, the second reading, in one embodiment, is taken at a wavelength from about 280 nm to about 700 nm, from about 280 nm to about 600 nm, from about 280 nm to about 500 nm, from about 280 nm to about 400 nm or from about 280 nm to about 350 nm. The absorbance measurement for the drug, in another embodiment, is taken at a wavelength from about 310 nm to about 700 nm, from about 350 nm to about 700 nm, from about 400 nm to about 700 nm, from about 450 nm to about 700 nm, from about 500 nm to about 700 nm, from about 550 nm to about 700 nm, from about 600 nm to about 700 nm or from about 650 nm to about 700 nm. In a further embodiment, the second (drug) reading is taken at about 300 nm, about 310 nm, about 320 nm, about 330 nm, about 340 nm, about 350 nm, about 360 nm, about 370 nm, about 400 nm, about 450 nm, about 500 nm, about 550 nm, about 600 nm, about 650 nm or about 700 nm.

As provided above, the first and second readings can be taken in any order.

In one embodiment, multiple drug molecules can be present in the sample, as described above. In this embodiment, the sample comprises multiple ADC populations, and the two drug molecules absorb light at two different wavelengths, and each drug molecule has a net charge associated with it. For example, one drug molecule might absorb light in the visible region while the second drug molecule might absorb light in the ultraviolet region of the electromagnetic spectrum. In another embodiment, each drug molecule might absorb light in the ultraviolet or both might absorb light in the visible region.

Absorbance readings are then taken for the drug molecules, as well as for the antibody. Therefore, three absorbance readings are taken. The protein absorbance reading is taken over a range of pI values, e.g., via a whole column detection method to determine the absorbance of each of the ADC species subpopulations in each ADC population. The cumulative ADC absorbance (i.e., the absorbance of each of the subpopulations of ADCs), in one embodiment, is compared to the absorbance value for each of the free drug molecules to determine the percentage of the individual free drugs in solution. Additionally, the cumulative ADC absorbance, in one embodiment, is compared to cumulative drug molecule absorbance, to determine the percentage of total free drug in the sample.

In one embodiment, one or more corresponding absorbance peaks (i.e., at one or more corresponding pI values) are compared between the readings to determine the number of drugs present in one or more ADC subpopulations. Here, the peaks are present at the pI value for the one or more ADC subpopulations.

The samples provided herein, in one embodiment, comprise at least one ADC species. As described above, ADC species can be differentiated on the basis of drug molecule bound to the antibody. For example, a first ADC species, in one embodiment, includes a drug with a higher net charge than a second ADC species.

Absorbance of the focused sample comprising the multiple species can then be measured at different wavelengths, as discussed above.

In another embodiment, multiple ADC species in a sample are distinguished based on the charge properties of the antibody. For example, one species of antibody, in one embodiment, has a higher net charge than a second species present in the sample. In this regard, the ADCs comprising the respective antibodies will migrate to different pIs.

Although the invention has been mainly described with samples comprising ADCs, the invention is not limited thereto. In one embodiment, the sample analyzed by the methods disclosed herein comprises a specific binding pair, wherein one of the specific binding pair members has a net charge.

Accordingly, in one embodiment, the methods provided herein comprise performing free solution isoelectric focusing on a sample comprising at least one specific binding pair population (e.g., in a capillary tube) to obtain a focused sample. One member of the specific binding pair, in one embodiment, is multimeric, i.e., it is able to bind multiple specific binding pair members. Absorbance of the sample is then measured at different wavelengths, for example two ultraviolet wavelengths, or one ultraviolet wavelength and one visible wavelength. One absorbance value is specific for the free (non-target) specific binding pair member, i.e., target specific binding pair absorbance is minimal to undetectable at one of the chosen wavelengths, e.g., from about 280 nm to about 700 nm, or about 280 nm to about 600 nm, or about 280 nm to about 500 nm, or about 280 nm to about 400 nm. In one embodiment, the absorbance reading for the free specific binding pair member (e.g., free charged antigen) is carried out over a range of pI values, by whole column detection. The absorbance values at individual pI values are compared to corresponding absorbance values at the second wavelength to determine the distribution of free and bound specific binding pair members.

In another embodiment, if the pI value of the free specific binding pair member is known, a single absorbance reading can be taken at that respective pI value.

The second reading, in one embodiment, is carried out at a wavelength where the other member (target specific binding pair member) of the specific binding pair absorbs light, e.g., from about 220 nm to about 300 nm. At this wavelength, drug molecule absorbance is not detectable or is minimal. The protein absorbance reading is taken over a range of pI values, e.g., via a whole column detection method to determine the absorbance of each of the specific binding pair species subpopulations present in the sample. In one embodiment, one specific binding pair species is present in the sample. In another embodiment, two specific binding pair species are present in the sample. The cumulative specific binding pair absorbance (i.e., the absorbance of each of the subpopulations of specific binding pairs), is then compared to the absorbance value of the free specific binding pair member to determine the percentage of free specific binding pair member in solution.

In one embodiment, a sample comprising a multimeric antibody-charged antigen complex (specific binding pair) is subjected to the methods provided herein. The subpopulations in the sample, when subjected to isoelectric focusing, will migrate according to how many charged antigens are bound to the multimeric antibody. Focused sample absorbance measurements can then be taken at two different wavelengths to determine the amount of free antigen in the sample as well as the distribution of bound and free antigen.

In one embodiment, a sample comprising receptor-charged ligand complexes can be subjected to the methods provided herein (i.e., a specific binding pair). In this regard, the subpopulations in the sample, when subjected to isoelectric focusing, will migrate according to how many charged ligands are bound to the receptor. Focused sample absorbance measurements can then be taken at two different wavelengths to determine the amount of free antigen in the sample as well as the distribution of bound and free antigen.

All documents, patents, patent applications, publications, product descriptions, and protocols which are cited throughout this application are incorporated herein by reference in their entireties for all purposes.

The embodiments illustrated and discussed in this specification are intended only to teach those skilled in the art the best way known to the inventors to make and use the invention. Modifications and variation of the above-described embodiments of the invention are possible without departing from the invention, as appreciated by those skilled in the art in light of the above teachings. It is therefore understood that, within the scope of the claims and their equivalents, the invention may be practiced otherwise than as specifically described.

The invention claimed is:

1. A method, comprising:
    performing isoelectric focusing on a sample containing an antibody-drug conjugate (ADC) species subpopulation to focus the ADC species subpopulation at an isoelectric point;
    detecting, at the isoelectric point, an optical peak at a first wavelength indicative of a drug;
    detecting, at the isoelectric point, an optical peak at a second wavelength indicative of an antibody; and
    determining, for the ADC species subpopulation, a number of drug molecules conjugated to each antibody of the ADC species subpopulation based on the optical peak at the first wavelength and the optical peak at the second wavelength.

2. The method of claim 1, wherein:
    the isoelectric point is from a plurality of isoelectric points;
    the ADC species subpopulation is from a plurality of ADC species subpopulations contained in the sample; and
    focusing the ADC species subpopulation includes performing isoelectric focusing on the sample such that each ADC species subpopulation from the plurality of ADC species subpopulations is focused at a different isoelectric point from the plurality of isoelectric points.

3. The method of claim 1, wherein:
    the isoelectric point is a first isoelectric point;
    the ADC species subpopulation is a first ADC species subpopulation;
    the sample contains a second ADC species subpopulation;
    performing isoelectric focusing on the sample causes the first ADC species subpopulation to be focused at the first isoelectric point and the second ADC species subpopulation to be focused at a second isoelectric point, the method further comprising:
    detecting, at the second isoelectric point, an optical peak at the first wavelength indicative of the drug;
    detecting, at the second isoelectric point, an optical peak at the second wavelength indicative of the antibody; and
    determining, for the second ADC species subpopulation, a number of drug molecules conjugated to each antibody based on the optical peak at the first wavelength detected at the second isoelectric point and the optical peak at the second wavelength detected at the second isoelectric point.

4. The method of claim 1, wherein the first wavelength is between 220 nm and 300 nm and the second wavelength is between 280 nm and 700 nm.

5. The method of claim 1, wherein:
    the sample contains the ADC species subpopulation and a quantity of free drug, the method further comprising:
    detecting an optical signal indicative of the quantity of free drug.

6. The method of claim 1, wherein:
    the ADC species subpopulation is from a plurality of ADC species subpopulations contained in the sample; and
    the sample contains the plurality of ADC species subpopulations and a quantity of free drug, the method further comprising:
    determining a cumulative quantity of drug conjugated within the plurality of ADC species subpopulations; and
    determining a percentage of the quantity of free drug in the sample.

7. The method of claim 1, wherein focusing the ADC species subpopulation includes performing capillary isoelectric focusing on a sample containing the ADC species subpopulation.

8. The method of claim 1, wherein:
    the drug is a first drug;
    the antibody is a first antibody;
    the ADC species subpopulation is a subpopulation of a first ADC species associated with the first drug;
    focusing the ADC species subpopulation includes performing isoelectric focusing on a sample containing the first ADC species and a second ADC species associated with a second drug; and
    the isoelectric point is a first isoelectric point, the method further comprising:
    detecting, at a second isoelectric point, an optical peak at a third wavelength indicative of the second drug;
    detecting, at the second isoelectric point, an optical peak at a fourth wavelength indicative of a second antibody; and
    determining for a subpopulation of the second ADC species having the second isoelectric point, a number of second drug molecules conjugated to each second antibody based on the optical peak at the third wavelength and the optical peak at the fourth wavelength.

9. A method, comprising:
    performing isoelectric focusing on a sample containing a plurality of subpopulations of an antibody-drug conjugate (ADC) such that at least two subpopulations of the ADC are separated by isoelectric point;
    detecting, at a first isoelectric point, an optical peak indicative of a drug;
    detecting, at a second isoelectric point, an optical peak indicative of the drug; and
    determining a number of drug molecules present in a first subpopulation of the ADC having the first isoelectric point based on the optical peak detected at the first isoelectric point; and
    determining a number of drug molecules present in a second subpopulation of the ADC having the second isoelectric point based on the optical peak detected at the second isoelectric point.

10. The method of claim 9, further comprising:
    detecting, at the first isoelectric point, an optical peak indicative of an antibody, the number of drug molecules present in the first subpopulation of the ADC determined based on the optical peak indicative of the antibody detected at the first isoelectric point.

11. The method of claim 9, further comprising:
    detecting, at the first isoelectric point, an optical peak indicative of an antibody, the number of drug molecules present in the first subpopulation of the ADC determined based on the optical peak indicative of the antibody detected at the first isoelectric point; and detecting, at the second isoelectric point, an optical peak indicative of the antibody, the number of drug molecules present in the second subpopulation of the ADC determined based on the optical peak indicative of the antibody detected at the second isoelectric point.

12. The method of claim 9, wherein the sample contains a quantity of free drug, the method further comprising:

determining the quantity of free drug in the sample based on the number of drug molecules present in the first subpopulation of the ADC and the number of drug molecules present in the second subpopulation of the ADC.

13. The method of claim 9, further comprising:

detecting a plurality of optical peaks, each optical peak indicative of a subpopulation of the ADC; and determining a cumulative quantity of drug conjugated to antibodies based on the plurality of optical peaks.

14. The method of claim 9, wherein the sample contains a quantity of free drug, the method further comprising:

detecting an optical peak indicative of the quantity of free drug; and determining the quantity of free drug in the sample based on a cumulative quantity of drug conjugated to antibodies and the optical peak indicative of the free drug.

15. The method of claim 9, wherein the sample contains a quantity of free drug, the method further comprising:

detecting an optical peak indicative of the quantity of free drug;

detecting a plurality of optical peaks indicative of a plurality of subpopulations of the ADC, the plurality of optical peaks indicative of the plurality of subpopulations of the ADC including the optical peak indicative of the drug detected at the first isoelectric point and the optical peak indicative of the drug detected at the second isoelectric point;

determining a cumulative quantity of drug conjugated to antibodies based on the plurality of optical peaks indicative of the plurality of subpopulations of the ADC; and determining the quantity of free drug in the sample based on the cumulative quantity of drug conjugated to antibodies and the optical peak indicative of the quantity of free drug.

16. A method, comprising:

performing isoelectric focusing on a sample containing a plurality of specific binding pair members and a plurality of target specific binding pair members, at least some of the plurality of target specific binding pair members having at least one specific binding pair member bound thereto, to focus the at least some of the plurality of target specific binding pair members into one or more isoelectric points;

detecting, at an isoelectric point from the one or more isoelectric points, an optical peak at a first wavelength indicative of the specific binding pair members;

detecting, at the isoelectric point from the one or more isoelectric points, an optical peak at a second wavelength indicative of the target specific binding pair members; and determining a number of specific binding pair members bound to each target specific binding pair member at the isoelectric point from the one or more isoelectric points based on the optical peak at the first wavelength and the optical peak at the second wavelength.

17. The method of claim 16, wherein the isoelectric point from the one or more isoelectric points is a first isoelectric point, the method further comprising:

detecting, at a second isoelectric point from the one or more isoelectric points, an optical peak at the first wavelength indicative of the specific binding pair members;

detecting, at the second isoelectric point, an optical peak at the second wavelength indicative of the target specific binding pair members; and determining a number of specific binding pair members bound to each target specific pair member at the second isoelectric point based on the optical peak detected at the second isoelectric point at the first wavelength and the optical peak detected at the second isoelectric point at the second wavelength.

18. The method of claim 16, wherein the specific binding pair member is a charged antigen.

19. The method of claim 16, wherein a first subpopulation of target specific binding pair members from the plurality of specific binding pair members has a first number of specific binding pair members bound thereto and a second subpopulation of target specific binding pair members from the plurality of specific binding pair members has a second number of specific binding pair members bound thereto.

20. The method of claim 16, wherein:

a first subpopulation of target specific binding pair members from the plurality of specific binding pair members has a first number of specific binding pair members bound thereto and is focused into a first isoelectric point from the one or more isoelectric points; and a second subpopulation of target specific binding pair members from the plurality of specific binding pair members has a second number of specific binding pair members bound thereto and is focused into a second isoelectric point from the one or more isoelectric points.

* * * * *